(12) United States Patent
Chin et al.

(10) Patent No.: US 6,344,048 B1
(45) Date of Patent: *Feb. 5, 2002

(54) REMOVABLE OCCLUSION SYSTEM FOR ANEURYSM NECK

(75) Inventors: Yem Chin, Burlington; Jennifer J. McCrory, Boston; Anthony R. Tremaglio, Jr., Brookline; Richard Hudson, Revere, all of MA (US)

(73) Assignee: SCIMED Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,084

(22) Filed: Apr. 28, 1999

Related U.S. Application Data

(62) Division of application No. 08/891,011, filed on Jul. 10, 1997, now Pat. No. 5,928,260.

(51) Int. Cl.[7] .............................................. A61M 29/00
(52) U.S. Cl. ....................................... 606/200; 606/159
(58) Field of Search ................................ 606/200, 194, 606/159; 604/107, 95, 104

(56) References Cited

U.S. PATENT DOCUMENTS

| | | | |
|---|---|---|---|
| 3,996,938 A | * 12/1976 | Clark, III | 606/200 |
| 4,416,028 A | 11/1983 | Ericksson et al. | 3/1.4 |
| 4,650,466 A | 3/1987 | Luther | 604/95 |
| 4,790,819 A | 12/1988 | Li et al. | 604/59 |
| 4,921,484 A | * 5/1990 | Hillstead | 606/194 |
| 4,994,071 A | 2/1991 | MacGregor | 606/194 |
| 5,034,001 A | 7/1991 | Garrison et al. | 604/53 |
| 5,370,660 A | 12/1994 | Weinstein et al. | 606/215 |
| 5,549,626 A | * 8/1996 | Miller et al. | 606/200 |
| 5,571,173 A | 11/1996 | Parodi | 623/1 |
| 5,690,671 A | 11/1997 | McGurk et al. | 606/200 |
| 5,725,521 A | 3/1998 | Mueller | 606/7 |
| 5,749,883 A | * 5/1998 | Halpern | 606/159 |
| 5,916,235 A | * 6/1999 | Guglielmi | 606/200 |
| 5,935,139 A | * 8/1999 | Bates | 606/200 |
| 6,059,814 A | * 5/2000 | Ladd | 606/200 |

FOREIGN PATENT DOCUMENTS

| | | |
|---|---|---|
| EP | 0 664 104 A2 | 7/1994 |
| WO | WO 96/14027 | 5/1996 |
| WO | WO 96/17645 | 6/1996 |
| WO | WO 96/18343 | 6/1996 |
| WO | WO 97/01368 | 6/1996 |

OTHER PUBLICATIONS

Portion of Article from *Endovascular Neurological Intervention*, pp. 23–24, admitted prior art.
"Endovascular Treatment of Experimental Aneurysms with Liquid Polymers: The Protective Potential of Stents", by Istvan Szikora, M.D., et al., *Neurosurgery*, vol. 38, No. 2, Feb. 1996, pp. 339–346.

* cited by examiner

*Primary Examiner*—David O. Reip
*Assistant Examiner*—Julian W. Woo
(74) *Attorney, Agent, or Firm*—Westman, Champlin & Kelly, P.A.

(57) ABSTRACT

A system for treating an aneurysm in a vessel includes a delivery device having a delivery portion suitable for delivery of embolic material. The delivery device is placed in a neck of the aneurysm and an expandable member is placed proximate the neck. The expandable member is expanded to overlie substantially the entire neck. Embolic material is delivered to the aneurysm with a delivery device. The expandable member is held over the neck to inhibit movement of the embolic material out of the aneurysm. Blood is allowed to flow out of the aneurysm, past the neck of the aneurysm, and through the vessel while the expandable member is held over the neck of the aneurysm.

18 Claims, 6 Drawing Sheets

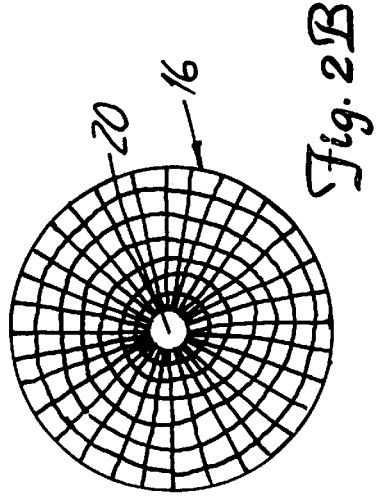
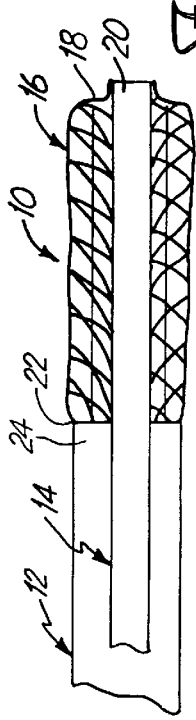
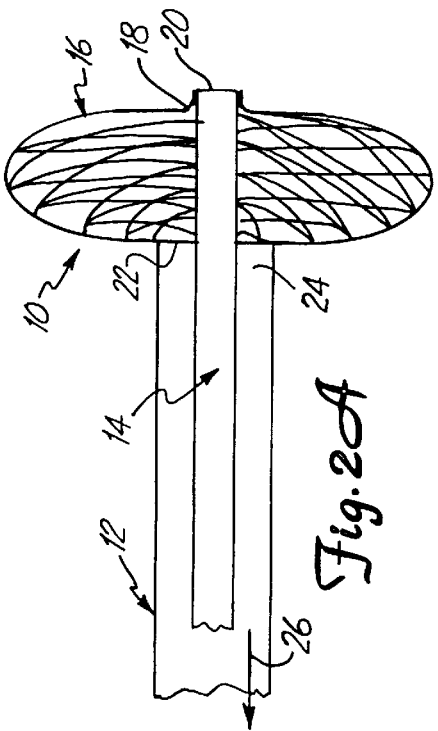
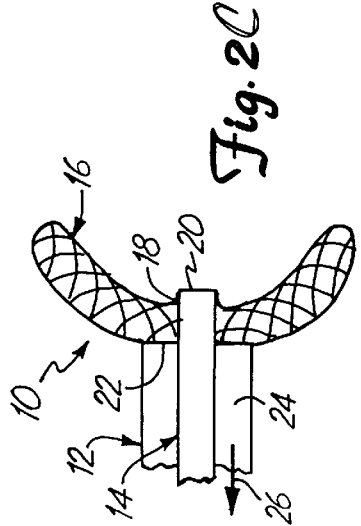
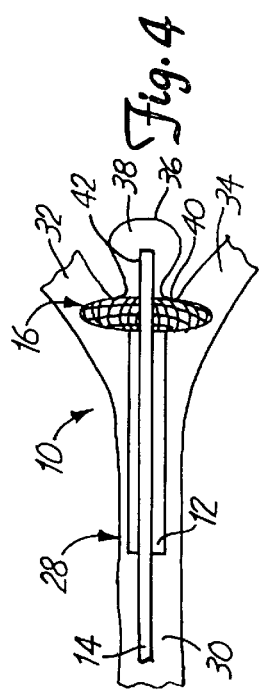
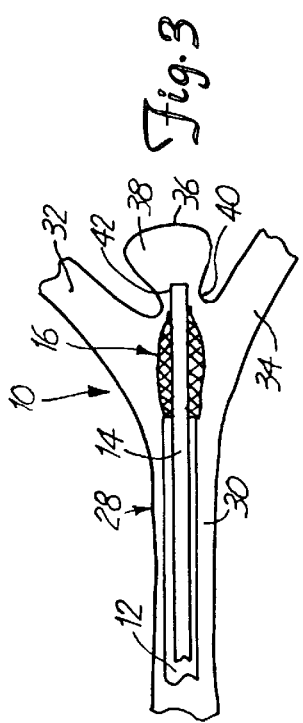

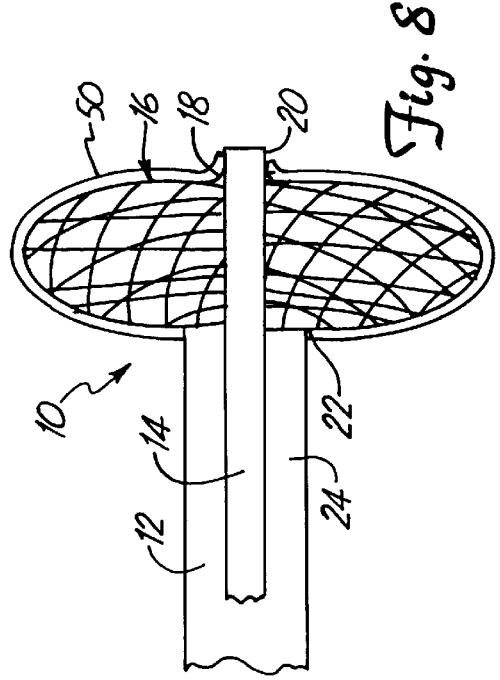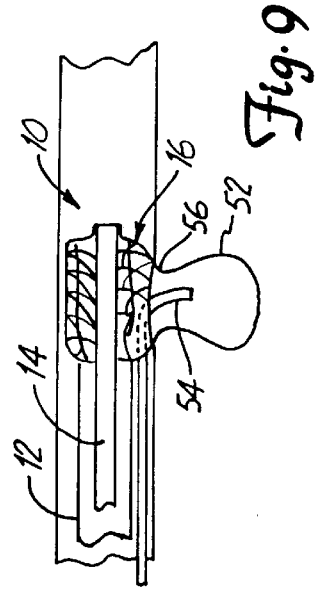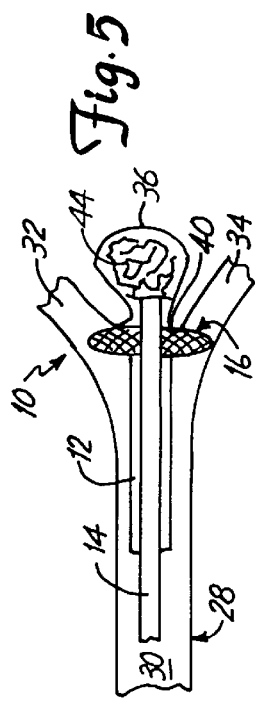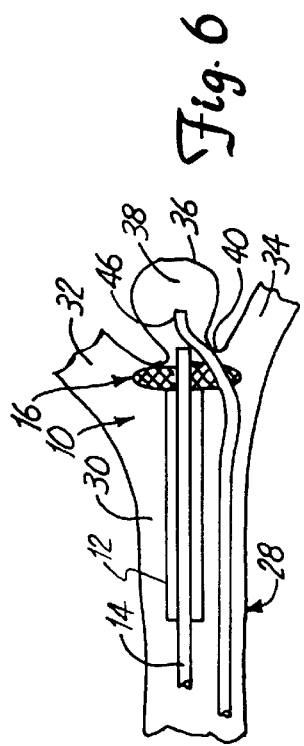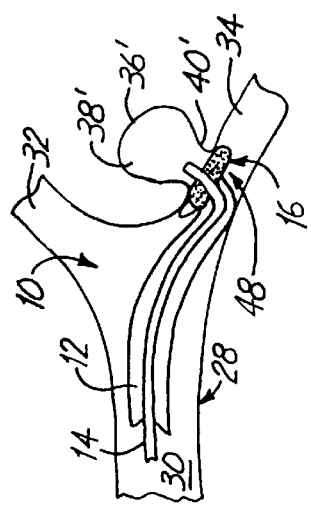

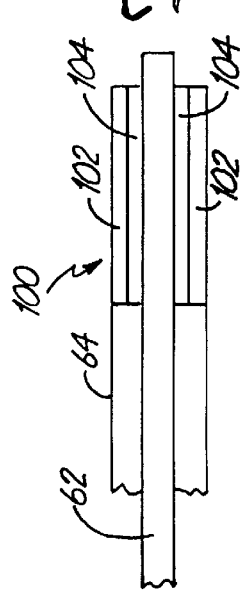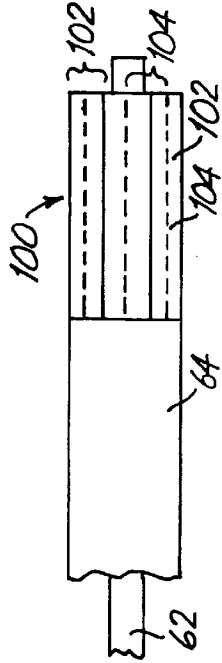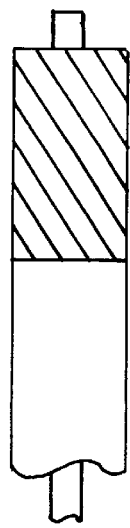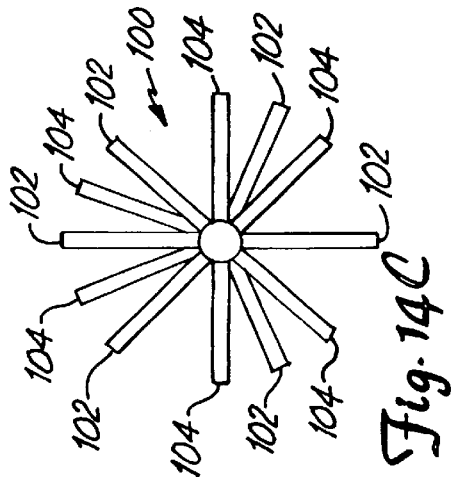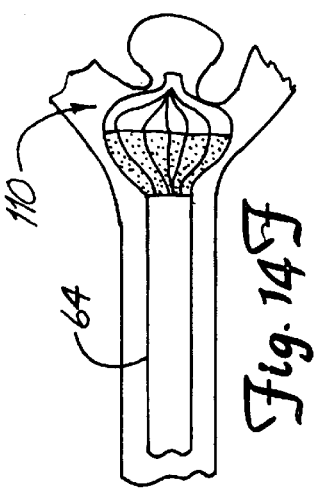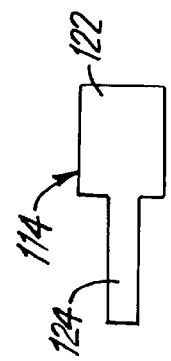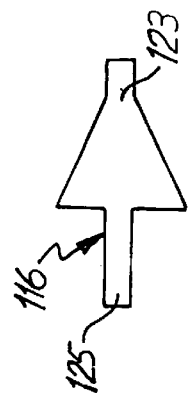

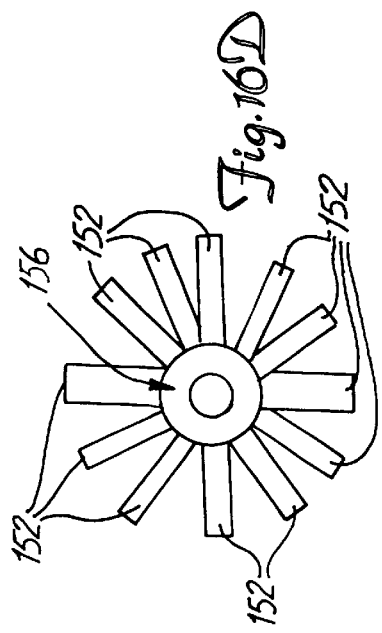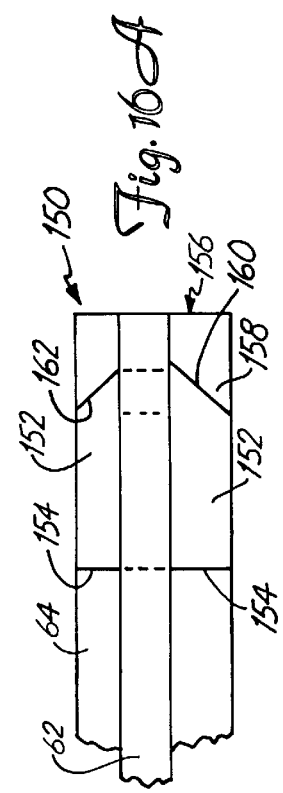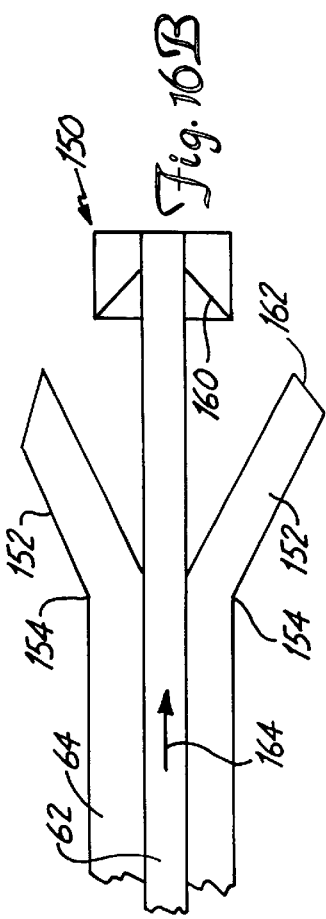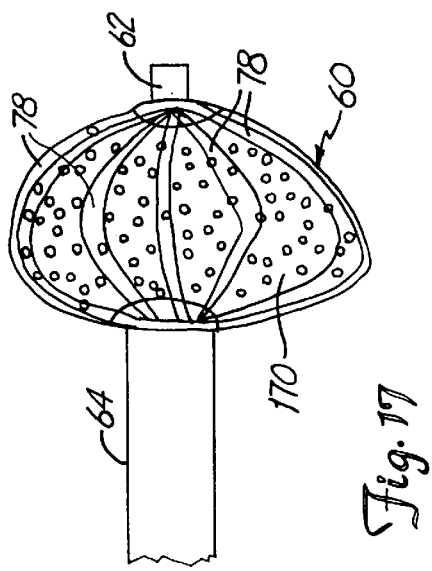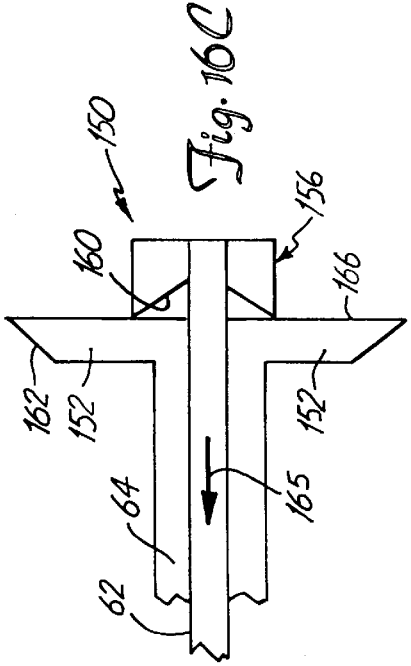

REMOVABLE OCCLUSION SYSTEM FOR ANEURYSM NECK

CROSS REFERENCE TO RELATED APPLICATION

This application is a divisional application of U.S. Ser. No. 09/891,011 filed Jul. 10, 1997 entitled REMOVABLE OCCLUSION SYSTEM FOR ANEURYSM NECK which issued as U.S. Pat. No. 5,928,260 on Jul. 27, 1999.

BACKGROUND OF THE INVENTION

The present invention deals with a system for treating an aneurysm. More specifically, the present invention deals with a removable occlusion system deployed in the vasculature containing the aneurysm.

Several methods of treating aneurysms have been attempted, with varying degrees of success. For example, open craniotomy is a procedure by which an aneurysm is located, and treated, extravascularly. This type of procedure has significant disadvantages. For example, the patient undergoing open craniotomy must undergo general anesthesia. Also, the patient undergoes a great deal of trauma in the area of the aneurysm by virtue of the fact that the surgeon must sever various tissues in order to reach the aneurysm. In treating cerebral aneurysms extravascularly, for instances, the surgeon must typically remove a portion of the patient's skull, and must also traumatize brain tissue in order to reach the aneurysm.

Other techniques used in treating aneurysms are performed endovascularly. Such techniques typically involve attempting to form a mass within the sac of the aneurysm. Typically, a microcatheter is used to access the aneurysm. The distal tip of the micro catheter is placed within the sac of the aneurysm, and the microcatheter is used to inject embolic material into the sac of the aneurysm. The embolic material includes, for example, detachable coils or an embolic agent, such as a liquid polymer. The injection of these types of embolic materials suffer from disadvantages, most of which are associated with migration of the embolic material out of the aneurysm into the parent artery. This can cause permanent and irreversible occlusion of the parent artery.

For example, when detachable coils are used to occlude an aneurysm which does not have a well defined neck region, the detachable coils can migrate out of the sac of the aneurysm and into the parent artery. Further, it is, at times, difficult to gauge exactly how full the sac of the aneurysm is when detachable coils are being injected. Therefore, there is a risk of overfilling the aneurysm in which case the detachable coils also spill out into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus, the aneurysm can recanalize.

Embolic agent migration is also a problem. For instance, where a liquid polymer is injected into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Some such techniques, commonly referred to as flow arrest techniques, typically involve temporarily occluding the parent vessel proximal of the aneurysm, so that no blood flow occurs through the parent vessel, until a thrombotic mass has formed in the sac of the aneurysm which helps reduce the tendency of the embolic material to migrate out of the aneurysm sac. However, thrombotic mass can dissolve through normal lysis of blood. Also, in certain cases, it is highly undesirable to occlude the parent vessel even temporarily. Therefore, this technique is, at times, not available as a treatment option. In addition, even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using saline and/or contrast fluid. The balloon is then detached from the microcatheter and left within the sac of the aneurysm in an attempt to fill the sac of the aneurysm. However, detachable balloons also suffer disadvantages. For example, detachable balloons, when inflated, typically will not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm. Further, detachable balloons can rupture and migrate out of the aneurysm.

SUMMARY OF THE INVENTION

A system for treating an aneurysm in a vessel includes a delivery device having a delivery portion suitable for delivery of embolic material. The delivery device is placed in a neck of the aneurysm and an expandable member is placed proximate the neck. The expandable member is expanded to overlie substantially the entire neck. Embolic material is delivered to the aneurysm with a delivery device. The expandable member is held over the neck to inhibit movement of the embolic material out of the aneurysm. Blood is allowed to flow out of the aneurysm, past the neck of the aneurysm, and through the vessel while the expandable member is held over the neck of the aneurysm.

BRIEF DESCRIPTION OF THE DRAWINGS

FIG. 1 is a side view of a portion of a neck occlusion device in accordance with the present invention.

FIGS. 2A and 2B are side and end views, respectively, of the neck occlusion device shown in FIG. 1 in an expanded position.

FIG. 2C is a side view of the device shown in FIG. 2A in an expanded position.

FIGS. 3–7 illustrate the deployment of the neck occlusion device shown in FIGS. 1, 2A and 2B during treatment of an aneurysm.

FIG. 8 illustrates a second embodiment of the neck occlusion device in accordance with the present invention.

FIG. 9 illustrates yet another embodiment of a neck occlusion device in accordance with the present invention.

FIGS. 16A–16D illustrate yet another embodiment of a neck occlusion device in accordance with the present invention.

FIG. 17 illustrates yet another embodiment of a neck occlusion device in accordance with the present invention.

DETAILED DESCRIPTION OF THE PREFERRED EMBODIMENTS

Figure 12:
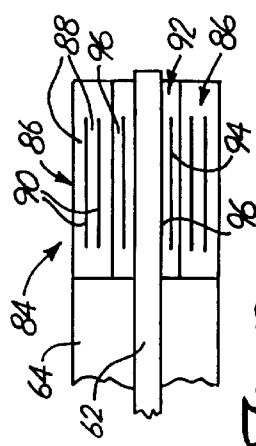
FIGS. 12–13B illustrate yet another embodiment of a neck occlusion device in accordance with the present invention.

FIG. 1 is a side view of a portion of a neck occlusion device 10 in accordance with the present invention. Device 10 includes outer tubular member 12, inner tubular member 14, and mesh portion 16. Tubes 12 and 14 are preferably coaxially arranged relative to one another, and are longitudinally slidable relative to one another. Mesh portion 16 is attached, at its distal end 18, to a distal portion 20 of inner tubular member 14. Mesh 16 is attached at its proximal end 22 to a distal portion 24 of outer tubular member 12.

Mesh portion 16 is preferably formed of braided or woven filaments or fibers which are relatively flexible. Therefore, when tubes 12 and 14 are moved relative to one another, mesh portion 16 is deployed radially outwardly relative to the tubes 12 and 14. This is illustrated by FIG. 2A.

FIG. 2A shows similar items to those shown in FIG. 1, and they are similarly numbered. However, in FIG. 2A, inner tube 14 has been retracted in the direction indicated by arrow 26 relative to outer tube 12. This causes the distal end 20 of inner tube 14 to approach the distal end 24 of outer tube 12. This also, consequently, causes the central portion of mesh 16 to deploy radially outwardly relative to the two tubular members 12 and 14 to form a substantially disk-shaped (or dish-shaped) configuration. It should also be noted that a pull wire can be alternatively implemented in place of tube 14. FIG. 2B is an end view of device 10 in the deployed position shown in FIG. 2A. However, FIG. 2B also shows that mesh portion 16 is relatively porous. This has advantages discussed with respect to FIGS. 3–7.

FIG. 2C illustrates device 10 with inner tube 14 even further retracted in the direction indicated by arrow 26 relative to outer tube 12. This causes mesh portion 16 to assume a general dish or concave shape. The present invention contemplates deployment of device 10 in this shape as well as in the other deployed shapes discussed herein.

FIGS. 3–7 illustrate the deployment of device 10 in treating an aneurysm. FIG. 3 shows a blood vessel 28 having a main lumen 30 which bifurcates into two branch lumens 32 and 34 which communicate with lumen 30. At a region proximate the transition from lumen 30 to branch lumens 32 and 34, aneurysm 36 has formed in the vessel wall. Aneurysm 36 has an interior sac portion 38 and a neck region 40. In order to treat aneurysm 36, FIG. 3 illustrates that device 10 is advanced through the vasculature, through lumen 30, to a region proximate the neck 40 of aneurysm 36. In the preferred embodiment, inner tube 14 has a distal extension portion 42 which extends beyond the distal end of mesh 16.

FIG. 4 illustrates that, once device 10 is placed in the region of neck 40 in the vasculature, mesh portion 16 is moved to its deployed (or radially expanded) position. This is done as described with respect to FIG. 2A, by moving tubes 14 and 16 longitudinally relative to one another to cause mesh portion 16 to deploy radially outwardly. FIG. 4 shows that, in the preferred embodiment, mesh portion 16, when deployed, substantially overlies the entire neck portion 40 of aneurysm 36.

FIG. 5 is similar to FIGS. 3 and 4, and similar items are similarly numbered. However, FIG. 5 illustrates that, once mesh portion 16 is deployed over the neck region 40 of aneurysm 36, embolic material 44 is placed in the interior sac 38 of aneurysm 36. In one preferred embodiment, the embolic material includes any suitable embolic material, such as coils, detachable coils, liquid embolic agents, or other suitable embolic material. The apertures in mesh portion 36 allow blood to migrate out of the sac portion 38 of aneurysm 36 upon being displaced in aneurysm 36 by embolic materials introduced into aneurysm 36. Also, device 10, when deployed, preferably has a low enough profile that it does not block any of lumens 30, 32 or 34. The porous nature of mesh portion 16 also allows blood to flow through vessels 30, 32 and 34 through mesh portion 16.

In the embodiment shown in FIG. 4, because aneurysm 36 is located in a region where lumen 30 bifurcates into lumens 32 and 34, mesh portion 16 may typically have a larger outer diameter than the inner diameter of lumen 30. In other words, mesh portion 16, when deployed, expands radially outwardly and extends down a portion of lumens 32 and 34. In being so formed, the outer diameter of mesh portion 16, in the deployed position, can be larger than the inner diameter of lumen 30. However, since mesh portion 16 collapses to the position shown in FIG. 3, it can be advanced and removed through vessel 30, yet still be deployed in a large enough configuration to substantially block the entire neck region 40 of aneurysm 36.

FIG. 6 shows another preferred way of placing embolic material 44 in the sac 38 of aneurysm 36. FIG. 6 illustrates that a microcatheter 46 has been advanced through lumen 30 and through the apertures in mesh portion 16. Of course, microcatheter 46 can also be placed in the sac 38 of aneurysm 36 prior to the deployment of mesh portion 16. In that case, when mesh portion 16 is deployed, it simply deflects a portion of microcatheter 46 out toward the wall of the neck region 40 of aneurysm 36, but does not exert enough pressure on microcatheter 46 to pinch off or close the lumen thereof. Therefore, embolic materials can still be advanced therethrough. It should also be noted that, in the embodiment shown in FIG. 6, where a separate microcatheter 46 is used to introduce embolic material into the sac 38 of aneurysm 36, the central tube 14 of device 10 need not be hollow, but can instead be a core wire device, or another suitable solid elongate member.

FIG. 7 illustrates device 10 as deployed in treating an aneurysm 36'. Aneurysm 36' is similar to aneurysm 36, except that it is offset from the region where lumen 30 bifurcates into lumens 32 and 34. However, it is only offset by a small distance. Therefore, device 10 can be maneuvered to have its distal tip within the sac 38' of aneurysm 36'. Also, it is offset by a distance which is small enough that longitudinal pressure applied to device 10 through tubes 12 and 14 causes deployed mesh portion 16 to abut and substantially overlie the neck region 40' of aneurysm 36'. It should be noted that the longitudinal force applied can cause mesh portion 16 to direct a force against the neck region 40 either directly, or by the tubes 12 and 14 backing up against lumen wall 48 which is substantially directly across from the opening in neck region 40' of aneurysm 36'. This causes tubes 12 and 14 to deflect toward the neck region 40' of aneurysm 36' and exert a force thereagainst.

FIG. 8 illustrates device 10 formed in accordance with another preferred embodiment of the present invention. In FIG. 8, a resilient material layer 50 is disposed over the outer radial surface of mesh portion 16. Resilient layer 50 is preferably a stretchy, woven material which has a number of apertures or perforations formed therein. However, the perforations are not as large as those which are formed in mesh portion 16, itself. Layer 50 thus provides the added advantage that mesh portion 16, when deployed, has a greater surface area facing neck region 40 of aneurysm 36. This enhances the ability of device 10 to deflect embolic material introduced into the sac 38 of aneurysm 36 back into aneurysm 36, and to keep it from migrating through neck portion 40 into the lumens 30, 32 or 34 of vessel 28. However, the perforations still allow blood from the sac 38 of aneurysm 36 to flow out into vessels 30, 32 or 34, upon being displaced by embolic materials introduced into the sac 38 of aneurysm 36.

FIG. 9 illustrates another method of using device 10 in accordance with the present invention. In the embodiment shown in FIG. 9, device 10 has substantially the same elements as that shown in FIG. 1. However, device 10 is configured to form a longer, wider tubular configuration when deployed radially outwardly, than that shown in FIGS. 2A, 4, 5 and 7. Thus, device 10 is more suitable for use in treating aneurysms, such as aneurysm 52, which is formed in a vessel wall that is not near a bifurcation in the vasculature. In the preferred embodiment shown in FIG. 9, microcatheter 54 is first introduced through neck region 56 of aneurysm 52 and into the sac of aneurysm 52. Then, device 10 is placed proximate neck region 56 and deployed to the expanded position shown in FIG. 9. Embolic material is then introduced through microcatheter 54 into aneurysm 52 and device 10 is in place to deflect back into aneurysm 52 substantially all embolic material which would otherwise tend to migrate through neck 56 into the parent vessel.

Alternatively, device 10 can first be introduced and placed proximate neck portion 56 of aneurysm 52 and maintained in the collapsed position. Microcatheter 54 is then introduced into aneurysm 52 and device 10 is then deployed outwardly. Also, as with the embodiment described in FIG. 6, mesh portion 16 of device 10 can be formed of a material having wide enough apertures that microcatheter 54 can be introduced therethrough. In that embodiment, it does not matter whether device 10 is first deployed, and then microcatheter 54 is inserted in aneurysm 52, or whether microcatheter 54 is first inserted in aneurysm 52 and then device 10 is deployed.

Of course, as with respect to device 10 shown in FIG. 8, the embodiment of device 10 shown in FIG. 9 can also be covered by a resilient material layer 50. Substantially the same advantages are achieved by such a covering layer as those achieved in the embodiment shown in FIG. 6.

It should further be noted that device 10 shown in FIG. 9 preferably has substantial perforations or apertures therein, when deployed. This serves two purposes. First, it allows blood to flow out of aneurysm 52 as it is displaced by an embolic material. Also, it allows blood to continue flowing through the parent vessel, and thus does not tend to cause occlusion of the parent vessel when deployed in the parent vessel.

In one preferred embodiment, mesh portion 16 is formed of woven strands of polymer material, such as nylon, polypropylene or polyester. The polymer strands can be filled with a radiopaque material which allows the physician treating the aneurysm to fluoroscopically visualize the location of mesh portion 16 within the vasculature. Radiopaque filler materials preferably include bismuth trioxide, tungsten, titanium dioxide or barium sulfate, or radiopaque dyes such as iodine. It should also be noted that mesh portion 16 can be formed by strands of radiopaque material. The radiopaque strands allow the physician to fluoroscopically visualize the location of mesh portion 16, without the use of filled polymer materials. Such radiopaque strands may preferably be formed of gold, platinum, or a platinum/iridium alloy.

In the embodiment in which mesh portion 16 is formed of radiopaque metal strands, it is preferred to cover the strands with a polymer coating or extrusion. The coating or extrusion over the radiopaque wire strands provides fluoroscopic visualization of mesh portion 16, but also increases the resistance of the strands to bending fatigue and may also increase lubricity of the strands. The polymer coating or extrusion, in one preferred embodiment, is coated or treated with an agent which tends to resist clotting, such as heparin. Such clot resistant coatings are generally known. The polymer coating or extrusion can be any suitable extrudable polymer, or any polymer that can be applied in a thin coating, such as teflon or polyurethane.

In yet another embodiment, the strands of mesh portion 16 are formed using both metal and polymer braided strands. Combining the metal strands with the polymer strands into a braid changes the flexibility characteristics of mesh portion 16. The force required to deploy or collapse such a mesh portion is significantly reduced over that required for a mesh portion that includes only metal mesh strands. However, the radiopaque characteristics of the mesh for fluoroscopic visualization are retained. Metal strands forming such a device preferably include stainless steel, gold, platinum, platinum/iridium or nitinol. Polymer strands forming the device can preferably include nylon, polypropylene, polyester or teflon. Further, polymer strands of mesh portion 16 can be chemically modified to make them radiopaque, such as by using gold deposition onto the polymer strands, or by using ion beam plasma deposition of suitable metal ions onto the polymer strands.

Mesh portion 16 can also be formed with filaments or strands of varying diameter and/or varying flexibility. By varying the size or flexibility of the polymer strands, the flexibility characteristics of mesh portion 16, upon deployment, can also be varied. By varying the flexibility characteristics, both the deployed and collapsed configuration of mesh portion 16 can be varied or changed to substantially any desired shape. As with previous embodiments, preferred materials for the strands include nylon, polypropylene, polyester and teflon.

Not only can mesh portion 16 be formed of both polymer strands or filaments and metal strands or filaments, but it can be formed using filaments of different polymer materials. For example, different polymer materials having different flexibility characteristics can be used in forming mesh portion 16. This alters the flexibility characteristics to change the resultant configuration of mesh portion 16 in both the deployed and the collapsed positions.

Figure 10:
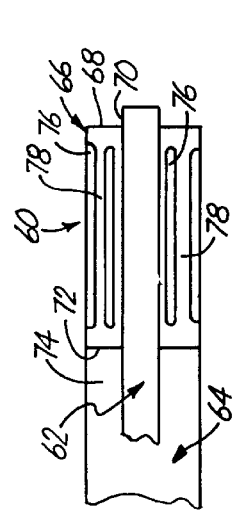

FIGS. 10–14I illustrate the present invention formed in the shape of a collapsing tube. FIG. 10 illustrates a portion of device 60 in accordance with the present invention. Device 60 includes inner tube 62 and outer tube 64. Tubes 62 and 64 are preferably coaxially arranged relative to one another. Collapsing tube portion 66 is coupled to inner tube 62 and outer tube 64. Collapsing tube portion 66 can be a separate member coupled to tubes 62 and 64, or it can be integrally formed with one or both of tubes 62 and 64. Collapsing tube portion 66 has a distal end 68 thereof which is attached to distal portion 70 of inner tube 62. Collapsing tube portion 66 also has a proximal end 72 which is attached to a distal region 74 of outer tube 64. In the embodiment shown in FIG. 10, collapsing tube 60 has a plurality of notches 76 formed therein. By forming notches 76, a plurality of struts 78 are defined therebetween and extend generally from the proximal end 72 of collapsing tube portion 66 to the distal end 68 thereof.

Figure 11C:
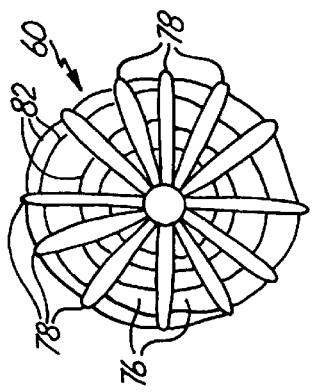
FIGS. 10–11D illustrate two additional embodiments of a neck occlusion device in accordance with the present invention.
Figure 11D:
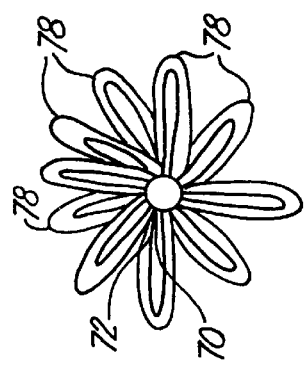
Figure 11A:
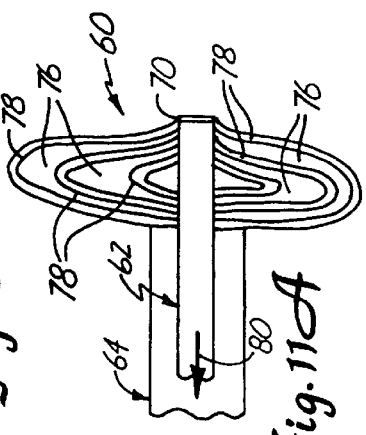

FIG. 11A illustrates device 60 in the deployed position. Tubes 62 and 64 are preferably longitudinally moveable relative to one another. Therefore, in order to deploy device 60, inner tube 62 is pulled in the direction generally indicated by arrow 80 relative to outer tube 64. This causes the distal end 74 of outer tube 64 to advance toward the distal end 70 of inner tube 62. This movement causes the struts 78 defined by notches 76 to bow or deploy generally radially outwardly, away from tubes 62 and 64 to the configuration shown in FIG. 11A.

Figure 11B:
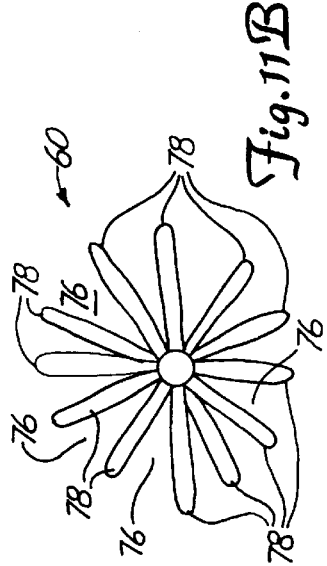

FIG. 11B illustrates an end view of device 60. FIG. 11B illustrates that struts 78 deploy radially outwardly in a flower pedal-like arrangement. Thus, notches 76 allow for the movement of blood out from within an aneurysm being treated by device 60 as it is replaced by embolic material, but struts 78 form deflecting surfaces to inhibit migration of the embolic material out of the aneurysm.

Thus, device 60 can be used in a similar fashion to device 10 shown in FIGS. 1–10 and discussed in greater detail above. However, device 60 provides struts 78 which typically have a larger constant surface area than the filaments forming mesh portion 16 of device 10. Thus, blood clotting may be less likely to occur around device 60. Also, the profile of device 60 in the collapsed position shown in FIG. 10 is typically slightly larger than the profile of mesh portion 16 when in the collapsed position shown in FIG. 1. However, device 60 is also typically less dense than mesh portion 16 when in the collapsed position and thus allows for easier blood flow around it during advancement or retraction in the vasculature.

FIG. 11C illustrates device 60 with a modification. Thread or suture material 82 is laced or threaded through struts 78 and across the spaces formed by notches 76 to create a mesh in notches 76. Suture material 82 thus provides additional surface area when device 60 is deployed. This additional surface area serves to enhance the ability of device 60 to deflect coils or other embolic material to keep it from migrating out of the aneurysm being treated. Any suitable type of polymer, thread, suture material, or other suitable polymer strands can be used to form thread 82.

FIG. 11D shows an end view of device 60 where outer tube 64 has been rotated with respect to inner tube 62. This causes the proximal ends of struts 78 to be rotated relative to the distal ends of struts 78 about the periphery of tubes 62 and 64. This type of rotation typically reduces the overall outer diameter of device 60 in the deployed position. It also changes the spacing between struts 78. In other words, the proximal ends of struts 78 are rotated to fill in a portion of the notches 76, when viewed from the distal end of device 60, to provide additional surface area for deflection of embolic material. Also, since the rotation of tubes 62 and 64 relative to one another changes the overall outer diameter of device 60 in the deployed position, this feature can be used in order to accommodate aneurysms having various neck sizes.

Figure 13A:
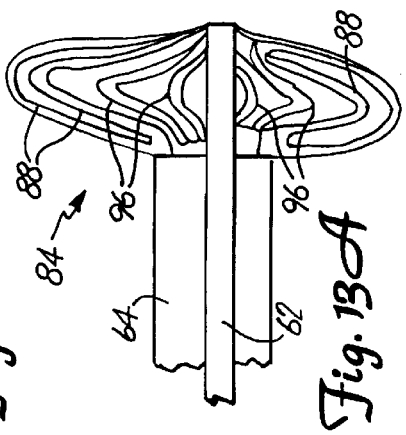
Figure 13B:
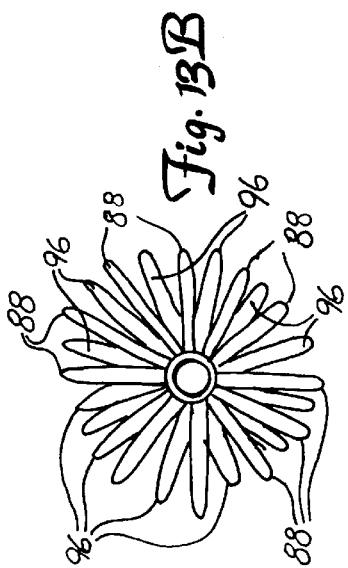

FIGS. 12–13B illustrate another embodiment of a sliced tube device in accordance with the present invention. FIG. 12 shows device 84 in a collapsed position. Device 84 is similar to device 60 in that a collapsing tube portion 86 has a plurality of struts 88 formed therein. However, instead of struts 88 being formed between notches or physical voids in tube portion 86, tube portion 86 simply includes a plurality of longitudinal slices 90 which define struts 88.

In addition, an inner collapsible tube portion 92 is also provided in device 84. Inner collapsible tube portion 92 is similar to outer collapsible tube portion 86, and is preferably coaxially arranged relative to outer tube portion 86. The outer tube 86 has an inner diameter which is slightly larger than the outer diameter of inner tube 92. Inner tube portion 92 also has a plurality of generally longitudinal cuts 94 formed therein to define inner struts 96. Outer collapsible tube portion 86 and inner collapsible tube portion 92 are preferably coupled to one another at their distal ends and to the distal end of inner tube 62. The proximal ends of inner and outer collapsible tube portion 86 and 92 are coupled to a distal region 74 of tube 64 and are slidable over inner tube 62.

FIG. 13A shows device 84 in the deployed position. Inner tube 62 is movable longitudinally within the interior of inner collapsible tube portion 92. Therefore, withdrawal of tube 62 relative to tube 64 causes both the distal ends of inner and outer collapsible tube portions 84 and 92 to advance toward their respective proximal ends. This causes the struts 88 and 96 to deploy radially outwardly as shown in FIG. 13A.

Also, in the preferred embodiment, struts 88 are angularly offset about the outer periphery of device 84 from inner struts 96. Therefore, when device 84 is deployed, the inner struts 96 deploy outwardly within the gaps left by the deployed outer struts 88. This is better illustrated in FIG. 13B which is an end view taken from the distal end of device 84 shown in FIG. 13A.

Devices 60 and 84 are preferably formed of any suitable material, such as PVC, polyurethane, low density polyethylene or nitinol. The design of the struts in devices 60 and 84 provide a relatively large and consistent surface area, with also relatively large amount of space between the deployed struts, when in the deployed position.

Figure 14J:
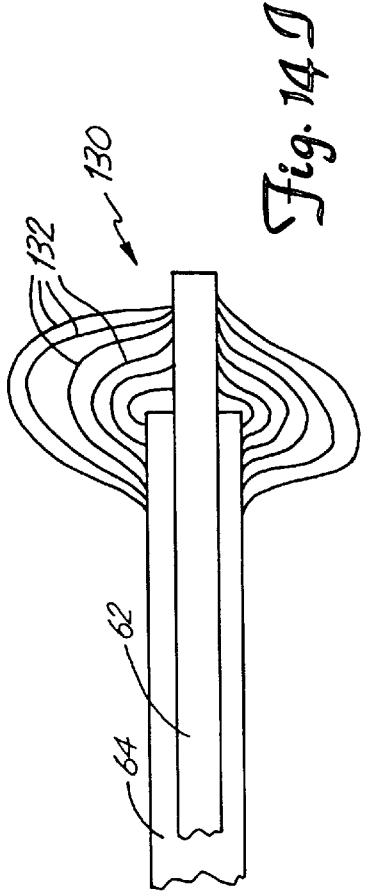
FIGS. 14A–14I illustrate additional embodiments of neck occlusion devices in accordance with the present invention.

FIGS. 14A, 14B and 14C illustrate another embodiment of the present invention. FIG. 14A is a side sectional view of device 100 and FIG. 14B is simply a side view of device 100 showing a plurality of strips 102 and 104. FIG. 14C illustrates device 100 in the radially deployed position. Device 100 is similar to devices 60 and 84. However, device 100 includes a plurality of strips or struts 102 which are formed, not by making longitudinal cuts or notches in the outer and inner tubes, but rather by adhering a plurality of discrete strips to the tubes.

In the embodiment shown in FIG. 14A, device 100 includes outer strips 102 and inner strips 104. Strips 102 are illustrated by the solid lines and strips 104 are illustrated by the dashed lines in FIG. 14B. It can be seen that strips 102 are radially located outside of, or over, strips 104 relative to the longitudinal axis of the inner tube 62. Strips 102 are adhered at distal ends thereof to inner strips 104 which are offset angularly relative to strips 102. Distal ends of strips 102 and 104 are not only connected to one another, but they are also connected to the distal end of inner tube 62. The proximal ends of strips 102 and 104 are not only adhered to one another, but are also adhered to the distal end of outer tube 64. Therefore, when tubes 62 and 64 are moved longitudinally relative to one another to bring their distal ends closer to one another, device 100 deploys radially outwardly as shown in FIG. 14C.

It should also be noted that, instead of flat strips of material, device 100 can be formed of threads or wires or other filamentous or fibrous material adhered or connected in the same manner as strips 102 and 104. As with the embodiment shown in FIGS. 12–13B, the preferred material for forming strips 102 and 104 includes PVC, polyurethane, low density polyethylene or nitinol. In the embodiment in which the strips are formed of wires or other filamentous material, any suitable monofilament polymer, suture material, nitinol or stainless steel, or any other suitable material, can be used. It should also be noted that the proximal and distal ends of strips 102 and 104, or the threads or fibers forming the struts, can be anchored around the tubes 62 and 64 using any suitable adhesive or other suitable connection technique.

Further, strips 102 and 104, or the wires forming those struts, can have their distal ends angularly offset about the circumference of tubes 62 and 64 relative to their proximal e:ids, and adhered that way. Such a device is shown in the collapsed position in FIG. 14D. This results, upon deployment, in device 100 substantially assuming the configuration shown in FIG. 11D, where the tubes are rotated relative to one another upon deployment of device 60. However, this configuration is obtained without the requirement of rotating tubes 62 and 64 relative to one another.

Devices 60, 84 or 100 can also be covered with the same type of resilient material as layer 50 shown in FIG. 8. Further, devices 84 and 100 can also have thread, suture material, polymer strands, or other suitable material laced therethrough to form a mesh, such as that shown in FIG. 11C.

It should also be noted that, in accordance with the present invention, the expandable devices can be formed having different characteristics along their length. For example, FIG. 14E illustrates a device 110 similar to device 100, which is formed by adhering strips of material 112 to tubes 62 and 64. The distal ends of the strips 112 used to form device 110 are solid, while the proximal ends thereof are perforated. As shown in FIG. 14F, device 110 thus has a proximal end which has significant additional perforations therein to allow blood flow therethrough in the parent vessel, yet has a distal end which has significantly fewer gaps or apertures therein to provide significantly more surface area for deflecting embolic material back into the sac of the aneurysm being treated.

However, the distal end of device 110 also has spaces between the strips or struts 112 to allow for the escape of blood from the aneurysm upon the insertion of embolic material therein.

This same type of affect can be accomplished using strips of material having different overall configurations. For example, FIGS. 14G and 14H illustrate strips 114 and 116 having a configuration wherein the distal ends 122 and 123 have a greater surface area than the proximal ends 124 and 125. Thus, devices formed with strips 114 or 116 yield a similar advantage to device 110. The distal end of the device formed with strips 114 or 116 has gaps or apertures therein which are smaller than those at the proximal end. This allows substantial additional blood flow through the proximal end but provides a greater deflecting surface at the distal end. It should also be noted that any of the strips 112, 114 or 116 can be partially or entirely perforated to provide substantial additional blood flow throughout the entire longitudinal length of a device formed by such strips.

FIG. 14I illustrates yet another embodiment of the present invention. In FIG. 14I, wires or filamentous strands 132 are used to form a device 130. The wires 132 have distal ends thereof attached to the inner tube 62 and proximal ends thereof attached to the outer tube 64. Wires 132 have different lengths. However, when tube 62 is fully extended within tube 64, such that the distal ends of the two tubes are separated from one another, wires 132 lay substantially flat against the outside of tubes 62 and 64 to approximate the outer diameters thereof. When tube 62 is retracted within tube 64 such that the distal ends approach one another, wires 132 deploy radially outwardly as shown in FIG. 14I.

FIGS. 15A–16D illustrate devices in accordance with yet another aspect of the present invention. The devices illustrated in these figures are self-expanding devices for treating an aneurysm. In general, the shape of the device is restrained in the collapsed (generally tubular) form for insertion into the vasculature and is then released to deploy radially outwardly.

Figure 15B:
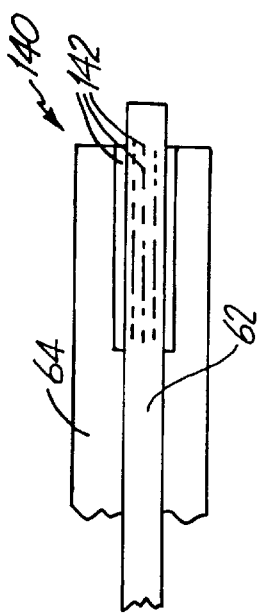
FIGS. 15A and 15B illustrate yet another embodiment of a neck occlusion device in accordance with the present invention.
Figure 15A:
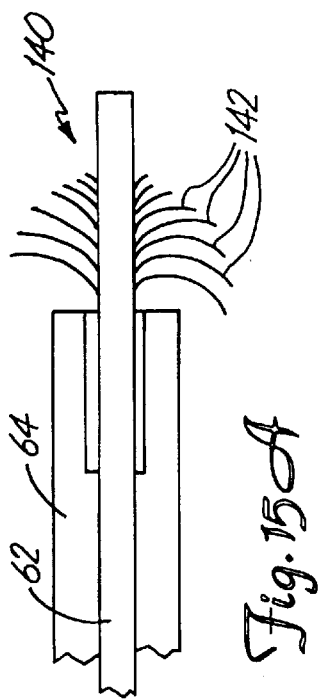

FIG. 15A illustrates device 140 in a deployed position. Device 140 includes inner tube 62 and outer tube 64. Polymer or metal wires or strands, or segments, 142 are set into a curved configuration and are attached at the proximal ends thereof about the outer circumference of inner tube 62. When unconstrained, wires 142 deploy radially outwardly as shown in FIG. 15A. Outer tube 64 has an inner diameter which approximates the outer diameter of tube 62. FIG. 15B shows that device 140 is retained in a collapsed, generally tubular shape, by outer tube 64 being advanced over wires 52 about inner tube 62. This urges wires 142 to straighten and lie generally flat against the outer surface of inner tube 62.

Strands 142 are preferably formed of any suitable material, such as nylon, teflon, polypropylene, nitinol, or stainless steel, and outer and inner tube 62 and 64 are also preferably formed of any suitable material, and can be formed of latex or polyurethane, or other suitable materials.

FIGS. 16A–16D illustrate another embodiment of a device 150 in accordance with the present invention. FIG. 16A illustrates that device 150 is formed of an inner tube 62 and an outer tube 64. Outer tube 64 has a distal end thereof split to form a plurality of expandable members 152, which are attached by a hinge connection 154 to the proximal portion of outer tube 64. Inner tube 62 has a radially enlarged hub 156 attached to the distal end thereof. Hub 156 has an annular, proximally extending ring 158. Ring 158 has a proximal end 160 which forms a retaining surface. Expandable members 152 of outer tube 64 each have a corresponding surface 162 at the distal end thereof. Surfaces 162 and surface 160 mate such that the distal ends of expandable members 152 are captured and retained in a radially collapsed position by surface 160 of hub 158.

In order to deploy device 150 into the radially expanded position, inner tube 62 (as shown in FIG. 16B) is advanced longitudinally with respect to outer tube 64 in the direction generally indicated by arrow 164. This causes surface 160 of hub 156 to come out of engagement with surfaces 162 of expandable members 152. Members 152 are preferably heatset at an outward angle relative to inner tube 62. Therefore, when surface 160 comes out of engagement with surfaces 162, the distal ends of expandable members 152 expand radially outwardly as shown in FIG. 16B.

FIG. 16C shows that once surfaces 160 and 162 are out of engagement with one another, and once members 152 have expanded radially outwardly as shown in FIG. 16B, inner tube 62 is withdrawn longitudinally relative to outer tube 64. This causes the annular ring terminating surface 160 to contact interior surfaces 166 of expandable members 152. By continuing to pull tube 62 in the direction indicated by arrow 165, hub 158 causes expandable members 152 to expand radially outwardly to the configuration shown in FIG. 16C. FIG. 16D is an end view of device 150 in the deployed position taken from the distal end of device 150.

In order to remove device 150 from the vasculature, inner tube 62 is again advanced distally with respect to outer tube 64 so that annular hub 156 is advanced to such a degree that surface 160 is out of engagement, and clear of, the interior surfaces 166 of expandable members 152. In this way, expandable members 152 can expand back radially inwardly with respect to tube 62 during removal of device 150 from the vasculature.

In the embodiment shown in FIGS. 16A–16D, inner shaft 62 is preferably formed of a suitable material, such as nylon, polyurethane or polyethylene. Outer tube 64 is preferably formed of any suitable material, such as latex or polyurethane.

FIG. 17 illustrates one additional aspect in accordance with the present invention. FIG. 17 illustrates that substantially any of the devices disclosed herein can be fully or partially covered with a perforated elastomeric sheath. FIG. 17 illustrates device 10 (shown in greater detail with respect to FIGS. 1–6) covered with elastomeric sheath 170. In the preferred embodiment, elastomeric sheath 170 creates additional surface area to deflect coils or other embolic material placed in the aneurysm being treated. In the preferred embodiment, elastomeric sheath 170 can be formed of any suitable material, such as latex or polyurethane.

As discussed above, inner tube 62 and outer tube 64 can be formed of any suitable material. However, inner tube 62, when used to deliver embolic material, preferably has an inner lumen with a polytetrafluoroethylene (PTFE) inner liner to provide lubricity for wire and coil movement therethrough. The PTFE inner liner is preferably applied by dipping the tube or extruding the liner onto the tube.

In addition, in one embodiment, tubes 62 and 64 are formed of a round or flat stainless steel coil which includes a dipped or extruded polymer jacket or overcoat layer with the PTFE inner liner. The coil can also be formed of round or flat platinum or platinum/iridium, gold or other suitable material.

Also, fiber braiding can optionally be substituted for, or used in addition to, the coil wire layer. Also, the braid or the wire coils may be interspersed at various locations along the longitudinal length of the tubes. This provides variable stiffness and flexibility zones along the longitudinal length of the tubes.

In addition, any wire coils which are used in the device can have centerless ground areas so that the wires themselves have multiple diameter zones smaller than the original diameter. This tapered wire is then wound to form the coil to provide variable stiffness zones along the longitudinal length of the catheter. This same type of grinding technique can be used with square or rectangular flat metal wire to provide the same benefits.

It has been found that metal coil layers add pushability, kink resistance, increased radiopacity, and increased burst strength to a composite tube material. The use of flat wire as compared to round wire improves the pushability, kink resistance and burst strength of the catheter or tube, but may cause the tube to be less flexible. Suitable polymer jacket materials for the tubes include nylon, polyurethane and polyethylene.

Further, the tubes 62 and 64 can be formed of multiple-polymer shafts consisting of a stiffer polymer in the proximal region and a more flexible polymer in the distal region. Additionally, different combinations of metal or polymer coils or braids, and different combinations of outer and inner jackets and sheaths can be employed to obtain different flexibility segments throughout the length of the tubes, as desired. Polyfusion extrusion techniques can also be used.

It should be noted that the devices described herein can be coated with a number of suitable coatings. Among the coatings which could be applied are growth factors. A number of suitable growth factors include vascular endothelial growth factor (VEGF), platelet derived growth factor (PDGF), vascular permeability growth factor (VPF), basic fibroblast growth factor (bFGF), and transforming growth factor beta (TGF-beta).

Although the present invention has been described with reference to preferred embodiments; workers skilled in the art will recognize that changes may be made in form and detail without departing from the spirit and scope of the invention.

What is claimed is:

1. A system for treating an aneurysm in a vessel, the aneurysm having a mouth communicating with the vessel, the system comprising:
   a first elongate tubular member including a first lumen extending therealong;
   a second elongate tubular member including a second lumen extending therealong and slidably disposed in the first lumen of the first elongate tubular member and longitudinally movable relative to the first elongate tubular member;
   a shield member having opposed first and second ends, the first end being coupled to the first elongate tubular member and the second end being coupled to the second elongate tubular member and the shield member operable between a first collapsed profile coaxially aligned with the first and second elongate tubular members and a second profile in response to longitudinal movement of the first and second elongate tubular members relative to one another, in the second profile, the shield member is angled relative to the longitudinal axis of the first and second elongate tubular members and the shield member including an inner layer and an outer layer covering the inner layer and expandable therewith, the inner layer forming a plurality of interspacial openings in the second profile and the outer layer being pervious to fluids; and
   wherein the shield member is configured in the second profile to cover the mouth of the aneurysm and the inner and outer layers inhibiting embolic material from moving out of the aneurysm into the vessel, and allowing blood to flow through the vessel and to flow out of the aneurysm during delivery of the embolic material into the aneurysm.

2. The system of claim 1 wherein the inner layer is formed of a mesh material.

3. The system of claim 2 wherein the mesh material is formed of one of radiopaque metal strands, or a polymer material.

4. The system of claim 2 wherein the outer layer is formed of a perforated elastomeric sheath.

5. The system of claim 1 wherein the outer layer is formed of a woven material.

6. The system of claim 1 wherein the inner layer is formed of a plurality of struts.

7. The system of claim 6 wherein the plurality of struts of include a proximal and distal portion along a length thereof, the distal portion having a larger surface area than the proximal portion for inhibiting fluid flow.

8. The system of claim 1 wherein the inner and outer layers include a plurality of struts.

9. The system of claim 8 wherein the inner and outer layers are formed of inner and outer collapsible tube portions forming the plurality of struts of the inner and outer layers.

10. The system of claim 9 and further comprising a micro catheter deployable to insert embolic material into the aneurysm having the mouth covered by the shield member.

11. A device for treating an aneurysm comprising:
   a first elongated member having a proximal and distal end;
   a second elongated member coaxially aligned with and slidable relative to the first elongated member and having a proximal and distal end;

a shield member having a first portion coupled proximate to the distal end of the first member and a second portion coupled proximate to the distal end of the second member and, the shield member being operable between a first collapsed profile coaxially aligned with the first and second members and a second profile angled relative to the longitudinal axis of the first and second members, the shield member being actuated between the first collapsed profile and the second profile via slidable movement of the first and second members, in the second profile, the shield member being configured to cover a mouth of an aneurysm and the shield member including an inner layer and an outer layer covering the inner layer and expandable therewith and the inner layer forming a plurality of interspacial openings in the second profile and the outer layer being pervious to fluids to permit blood flow through the shield member; and an embolic delivery lumen adapted to extend through a mouth of an aneurysm covered by the shield member in the second profile for inserting an embolic material into an aneurysm.

12. The device of claim 11 wherein the first member is a tubular member and the embolic delivery lumen is formed through a center conduit of the tubular member.

13. The device of claim 11 wherein the embolic delivery lumen is formed through a tubular member coaxially inserted with the first and second members.

14. The device of claim 11 wherein the inner layer is formed of a mesh material.

15. The device of claim 14 wherein the mesh material forms a concave shape in the second profile to cover a mouth of an aneurysm.

16. The device of claim 14 wherein the mesh material forms a relatively flat shape in the second profile to cover a mouth of an aneurysm.

17. The device of claim 14 wherein the mesh is formed of woven strands of polymer material filled with a radiopaque material.

18. The device of claim 14 wherein the mesh is formed of braided metal and polymer strands.

* * * * *

UNITED STATES PATENT AND TRADEMARK OFFICE
CERTIFICATE OF CORRECTION

PATENT NO. : 6,344,048 B1
DATED : February 5, 2002
INVENTOR(S) : Yem Chin et al.

It is certified that error appears in the above-identified patent and that said Letters Patent is hereby corrected as shown below:

Column 12,
Line 60, after "insert" insert -- the --.
Lines 63 and 67, after "proximal" insert -- end --.
Lines 63 and 67, after "and" insert -- a --.

Column 13,
Lines 12, 20 and 22, delete "an" and insert -- the --.
Line 19, delete "a" and insert -- the --.

Column 14,
Lines 11 and 14, delete "cover a" insert -- cover the --.
Lines 12 and 15, delete "an" and insert -- the --.
Lines 16 and 19, after "mesh" insert -- material --.

Signed and Sealed this

Ninth Day of August, 2005

JON W. DUDAS
*Director of the United States Patent and Trademark Office*